US009481620B2

(12) United States Patent
Benje et al.

(10) Patent No.: US 9,481,620 B2
(45) Date of Patent: Nov. 1, 2016

(54) PROCESS AND APPARATUS FOR HEAT RECOVERY IN VINYL CHLORIDE MONOMER PLANTS OR IN INTEGRATED VINYL CHLORIDE MONOMER OR POLYVINYL CHLORIDE PLANTS

(71) Applicants: THYSSENKRUPP INDUSTRIAL SOLUTIONS AG, Essen (DE); VINNOLIT GMBH & CO. KG, Burgkirchen (DE)

(72) Inventors: Michael Benje, Bad Soden (DE); Peter Kammerhofer, Burgkirchen (DE)

(73) Assignee: ThyssenKrupp Industrial Solutions AG, Essen (DE)

( * ) Notice: Subject to any disclaimer, the term of this patent is extended or adjusted under 35 U.S.C. 154(b) by 0 days.

(21) Appl. No.: 14/363,196

(22) PCT Filed: Nov. 15, 2012

(86) PCT No.: PCT/EP2012/004747
§ 371 (c)(1),
(2) Date: Jun. 5, 2014

(87) PCT Pub. No.: WO2013/083230
PCT Pub. Date: Jun. 13, 2013

(65) Prior Publication Data
US 2014/0336426 A1 Nov. 13, 2014

(30) Foreign Application Priority Data

Dec. 8, 2011 (DE) .................. 10 2011 120 479
Apr. 13, 2012 (DE) .................. 10 2012 007 339

(51) Int. Cl.
C07C 17/383 (2006.01)
B01J 19/00 (2006.01)
C07C 17/25 (2006.01)
B01D 3/00 (2006.01)
B01D 3/14 (2006.01)

(52) U.S. Cl.
CPC ............ *C07C 17/383* (2013.01); *B01D 3/007* (2013.01); *B01D 3/143* (2013.01); *B01J 19/0033* (2013.01); *C07C 17/25* (2013.01); *B01J 2219/00006* (2013.01); *B01J 2219/00076* (2013.01); *B01J 2219/00103* (2013.01); *Y02P 20/124* (2015.11); *Y02P 20/51* (2015.11); *Y02P 20/57* (2015.11); *Y02P 70/34* (2015.11)

(58) Field of Classification Search
CPC .. C07C 17/383; C07C 17/25; B01J 19/0033; B01J 2219/00006; B01J 2219/00103; B01J 2219/00076; B01D 3/007; B01D 3/143; Y02P 20/51; Y02P 20/57; Y02P 70/34
USPC ......................................... 570/262; 423/187
See application file for complete search history.

(56) References Cited

U.S. PATENT DOCUMENTS 4,747,914 A * 5/1988 Schwarzmaier et al. ....... 203/22

FOREIGN PATENT DOCUMENTS

| DE | 3519161 A1 | 12/1986 |
| DE | 102006062885 A1 | 12/2008 |
| EP | 0131932 A1 | 1/1985 |
| GB | 2457186 | * 12/2008 |

OTHER PUBLICATIONS

German Language International Search Report for International PCT Patent Application No. PCT/EP2012/004747; mailing date Feb. 1, 2013.
English translation of International Search Report for International PCT Patent Application No. PCT/EP2012/004747; mailing date Feb. 1, 2013.
Johann Stichlmair, et al., Reduction of Energy Requirements in Distillation, Chem. Eng. Technol. 12 (1989), pp. 163-169.

* cited by examiner

Primary Examiner — Shailendra Kumar
(74) Attorney, Agent, or Firm — Lathrop & Gage LLP

(57) ABSTRACT

Disclosed is a process and apparatus for heat recovery in vinyl chloride monomer manufacturing plants or in integrated vinyl chloride monomer/polyvinyl chloride manufacturing plants. A process for capture and use of excess heat recovered in the production of vinyl chloride includes distillatively purifying DCE in a high-boilers column, using a heat exchanger to capture thermal energy from a purified DCE vapor stream from the high-boilers column, generating low pressure steam from the captured thermal energy, returning condensed DCE vapors to the high-boilers column, and heating parts of the plant with the generated low pressure steam.

11 Claims, No Drawings

PROCESS AND APPARATUS FOR HEAT RECOVERY IN VINYL CHLORIDE MONOMER PLANTS OR IN INTEGRATED VINYL CHLORIDE MONOMER OR POLYVINYL CHLORIDE PLANTS

CROSS REFERENCE TO RELATED APPLICATIONS

This application is a U.S. National Stage Entry of, and claims priority to, International Patent Application Serial Number PCT/EP2012/004747, filed Nov. 15, 2012.

FIELD

This invention relates to a process for the capture and use of excess heat recovered during the production of vinyl chloride.

BACKGROUND

DCE is predominantly used as an intermediate to produce vinyl chloride monomer which in turn is used as starting material to produce polyvinyl chloride. The conversion of DCE into vinyl chloride monomer also produces hydrogen chloride HCl. HCl is preferably used to produce DCE by oxychlorination of ethene with HCl and oxygen. An alternative route to DCE is via the direct chlorination of ethene with chlorine. Both routes are taken in the large-scale industrial production of DCE, so the hydrogen chloride produced and the hydrogen chloride consumed balance in accordance with the following reaction equations:

$$Cl_2 + C_2H_4 \rightarrow C_2H_4Cl_2 + 218 \text{ kJ/mol}$$

$$C_2H_4Cl_2 \rightarrow C_2H_3Cl + HCl - 71 \text{ kJ/mol}$$

$$C_2H_4 + 2HCl + \tfrac{1}{2}O_2 \rightarrow C_2H_4Cl_2 + H_2O + 238 \text{ kJ/mol}$$

A plant complex for manufacture of vinyl chloride monomer (hereinafter called "VCM complex") consists essentially of:
- a plant for producing 1,2-dichloroethane (DCE) from ethene and chlorine ("direct chlorination", an optional plant component); and
- a plant for producing 1,2-dichloroethane from ethene, hydrogen chloride and oxygen ("oxychlorination"); and
- a plant for distillative purification of 1,2-dichloroethane (production of feed DCE); and
- a plant for thermally cracking the distillatively purified feed DCE into vinyl chloride and hydrogen chloride; and
- a plant for distillative removal of hydrogen chloride and of unconverted 1,2-dichloroethane and also for purification of vinyl chloride monomer.

The hydrogen chloride obtained by thermally cracking the 1,2-dichloroethane is returned into the oxychlorination plant and again reacted therein with ethene and oxygen to form DCE.

The reaction steps of direct chlorination and of oxychlorination are highly exothermic, whereas the thermal cracking of DCE into VCM and hydrogen chloride is endothermic.

The VCM complex described above can be operated in the balanced mode wherein all the DCE produced in the plant is also further processed in the VCM plant, and/or there is no need to import DCE.

In addition to the aforementioned balanced mode of operation, there are also modes/plants for producing DCE where the DCE quantity which would be manufactured in the direct chlorination step of the balanced mode is wholly or partly replaced by imported DCE. This operating mode or plant configuration is known as unbalanced among those skilled in the art.

There is a further unbalanced method of operation wherein the DCE-producing component plant produces more DCE than is consumed in the thermal cracking to VCM.

This excess DCE is subjected to distillative purification and then commercialized as "sales DCE". The "sales-DCE" mode generally employs more columns to work up the DCE than the other modes. These additional columns represent additional heatsinks and can be operated with heat from other parts of the plant.

Numerous measures to save energy/recover heat in VCM and PVC production plants are known from the prior art. Measures of this type lead to a distinct reduction in operating costs and hence make a very substantial contribution to the economic viability of the plant. Measures of this type similarly also make a significant contribution to cutting the plant's $CO_2$ output.

They also include measures whereby the reaction heat evolved by exothermic reaction steps is used to supply heat to heatsinks in the process. For instance, the reaction heat evolved by the oxychlorination reaction is used to generate steam which can be used, for example, to heat reactant preheaters or distillation columns.

Owing to the relatively high temperature level of the oxychlorination reaction, the generated steam is suitable for heating most of the heatsinks in the process. It will be appreciated that this steam is preferably used to supply heat to heatsinks which themselves require a relatively high temperature level.

The steam quantity generated in the oxychlorination plant is insufficient to heat all the heatsinks in a plant complex for production of VCM. Further heat recovery/energy saving options were accordingly sought.

One possibility is to use reaction heat from the direct chlorination reaction, which is obtained at a lower temperature level than that of the oxychlorination reaction. There are a multiplicity of proposals for this in the literature.

DE 32 25 732 A1, for instance, proposes using a recirculating stream of the liquid reaction medium from the direct chlorination step to heat a distillation column.

DE 31 37 513 A1 proposes using the reaction heat for space-heating purposes or for steam generation. However, there is a caveat with regard to steam generation via the reaction heat from the direct chlorination step in that the reaction temperature has to be raised for this to a value which in itself severely favors the formation of by-products, which in turn compromises the economic viability of the process. One way out would be for vaporous reaction medium from the direct chlorination reactor to be mechanically compressed and then used for heating purposes, as proposed in WO 01/21564 A1. This is disadvantageous because of the capital costs for the compressors needed as well as the energy costs for the compressing operation.

Existing proposals further include heating columns with vaporous reaction medium, as described in DE 199 16 753 C1 and WO 98/01407 A1 for example, and also simultaneously with vaporous and liquid reaction medium, as described in DE 199 53 762 A1.

Since direct chlorination plants and plant complexes for production of vinyl chloride monomer and vinyl chloride polymer are often integrated with a plant for chlor-alkali electrolysis, it has also been proposed to use the reaction heat of the direct chlorination reaction to concentrate aqueous sodium hydroxide solution, as described in DE 10 2005 044 177 A1 for example.

There are also energy-saving opportunities within the plant component dedicated to the distillative purification of 1,2-dichloroethane. This plant component within a VCM complex generally consists of a so-called dewatering column in which water as well as low boilers are removed from the DCE. Depending on the plant configuration, the plant may employ one or more further columns, for example for removing low boilers. The bottoms stream from the dewatering column is generally further purified in a so-called high-boilers column or DCE column. Furthermore, DCE removed from the product mixture of the thermal DCE cracking (so-called return DCE) is fed into the high-boilers column. Substances boiling higher than DCE are removed in the high-boilers column. The overhead product of the high-boilers column is the feed DCE for the thermal DCE cracking. The bottoms stream from the high-boilers column is usually further concentrated in a column operated under reduced pressure, i.e., a so-called vacuum column. The DCE removed in the vacuum column is admixed to the feed DCE stream from the top of the high-boilers column. The removed high boilers are sent to a workup stage.

The high-boilers column is the largest consumer of energy within the distillative DCE purification stage. In principle, the amount of heat recoverable in the direct chlorination plant is insufficient to cover the total energy requirements of this column. The missing heat has to be supplied by heating with steam. Nor is the high-boilers column vapor temperature attainable on heating the high-boilers column with the direct chlorination reaction heat sufficient to make the recovery of heat from the vapor economically viable.

SUMMARY

This invention relates to a process and apparatus for production of 1,2-dichloroethane (hereinafter "DCE"), and aims to operate a 1,2-dichloroethane distillation column at temperatures sufficient to produce usable heat by condensing at least part of the overhead stream (vapor) from the column, yet not so high as to cause damage to the distilled DCE due to thermal decomposition.

Specifically, this invention aims to use the thermal energy recovered at the top of a distillation column to supply heat to heatsinks in a plant for production of vinyl chloride monomer or in an integrated plant for production of vinyl chloride monomer (hereinafter "VCM") and polyvinyl chloride (hereinafter "PVC").

DETAILED DESCRIPTION

The present invention is directed to a process for heat recovery at the high-boilers column(s) (often also called "DCE column") of that plant component within a VCE complex that is dedicated to the distillative purification of DCE.

DE 34 40 685 A1 already proposed in this regard that the vapor from the top of this column be mechanically compressed and used for heating the selfsame column. However, it is energetically more favorable to operate the high-boilers column at a sufficient pressure and/or temperature that the overhead stream (vapor) from the column is suitable for implementing heat recovery measures. On the other hand, the overhead temperature of the column must not be so high as to cause the product (feed DCE) to be damaged by decomposition.

DE 35 19 161 A1 describes a process for purifying DCE, in which a distillation column is operated in such a way that a temperature at the top of 125-180° C. results. The gaseous DCE discharged at the top of this column is passed through heat exchangers which serve to heat DCE-containing product streams. The DCE condensed in the heat exchangers is then returned to the column and is partly discharged as purified product and reused. The process described increases the energy efficiency of the plant considerably. Nevertheless, the total thermal energy present in the overhead product cannot be utilized, but instead the DCE stream condensed in the heat exchangers has to be actively cooled. It would be desirable for the heat content of the overhead product from the high-boilers column, which has hitherto not been utilized, also to be able to be used for heating plant components.

It transpired that, surprisingly, the high-boilers column can be operated at overhead temperatures between about 120-150° C., preferably between 127 and 135° C., without any damage to the product being observed. For this, the high-boilers column is operated under superatmospheric pressure, for example in the range from 2.7 to 5.3 bar absolute and the vapors thus generated are used to obtain low-pressure steam which is used for indirect heating of components of the DCE plant or of components of the downstream VCM plant and/or PVC plant.

In the indirect heating of plant components of the DCE plant, the VCM plant and/or the PVC plant, it has been found that the entire useable heat content of the vapors from the high-boilers column(s) can be utilized by producing low-pressure steam. The generation of low-pressure steam is also preferred for heating physically further-removed heat-sinks for safety reasons. The generation of low-pressure steam from the vapors from a high-boilers column operated under superatmospheric pressure in a DCE plant has hitherto not been described.

The present invention provides a process for production of vinyl chloride by thermal cleavage of 1,2-dichloroethane in a vinyl chloride complex incorporating a distillative purification of 1,2-dichloroethane comprising at least one high-boilers column in which substances boiling higher than 1,2-dichloroethane are removed and incorporating an optionally attached polyvinyl chloride plant, said process involving the measures of
  a) operating the high-boilers column at overhead temperatures between 120-150° C., and
  b) using at least part of the overhead stream from the high-boilers column to obtain thermal energy used in heatsinks of a plant component dedicated to producing 1,2-dichloroethane, and/or in heatsinks of a downstream plant component dedicated to producing vinyl chloride, and/or in heatsinks of a downstream plant component dedicated to producing polyvinyl chloride, with
  c) the overhead stream being used for indirect heating of heatsinks by using at least part of the overhead stream from the high-boilers column to generate low-pressure steam and returning the overhead stream into the high-boilers column following condensation with or without supercooling and using the low-pressure steam for heating selected parts of the plant.

For the purposes of the present description, low-pressure steam is steam which typically has a temperature in the range from 115 to 145° C., preferably from 118 to 130° C.

The overhead stream is used for indirect heating of heatsinks by using at least part of the overhead stream from the high-boilers column to generate low-pressure steam, for example in a heat exchanger such as an evaporator, and returning the overhead stream into the high-boilers column following condensation with or without supercooling and using the low-pressure steam for heating selected parts of the plant. This method is preferable for heating plant components far removed from the high-boilers column, for example for heating heatsinks in a downstream VCM plant and/or a downstream PVC plant.

Any type of common heat exchanger can be used for the indirect heating of heatsinks. Particular preference is given to heat exchanger types which enable heat to be transferred at particularly low temperature differences between the hot side and the cold side. Very particular preference here is given to falling-stream evaporators, plate-type heat exchangers, coil-type heat exchangers or tube-bundle heat exchangers, the latter being fitted with tubes specifically suitable for heat exchange at low temperature differences (e.g., "high-flux" tubes from Honeywell UOP, Houston Tex., USA).

Suitable and preferred heatsinks in a plant complex for VCM/PVC production are:

In the VCM complex:
dewatering column;
low-boilers column or DCE stripper;
vacuum column;
boiler feed water devolatilizer;
stripping column for removing DCE from wastewater; and
stripping column for purifying (removing HCl) vinyl chloride.

In the PVC plant:
apparatuses for removing residual monomer (VCM) from PVC, specifically a predevolatilizing device and a downstream devolatilizing column;
stripping column for removing VCM from wastewater;
apparatus for drying PVC powder; and
apparatus for heating batch water for the polymerization reaction.

The process according to the invention is distinguished by the fact that the indirect heating of heatsinks is carried out with low-pressure steam generated from the overhead stream from the high-boilers column of the DCE plant.

Preference is given to a process for production of vinyl chloride and polyvinyl chloride wherein the bottom product from the high-boilers column has a DCE content of 90-97 wt %.

In a preferred process variant, the DCE purified by distillation in the high-boilers column is used without further treatment for the thermal dissociation to form vinyl chloride.

The operation of the high-boilers column and of the attached heat exchangers can surprisingly be carried out without interruption for a long time. Thus, uninterrupted operation for from 6 to 24 months is quite possible without cleaning of these plant components being necessary during this time.

The invention further provides a process in which the high-boilers column is operated without interruption for from six to twenty-four months.

The invention also provides apparatus for production of vinyl chloride by thermal cleavage of 1,2-dichloroethane in a vinyl chloride complex incorporating a distillative purification of 1,2-dichloroethane and an optionally attached polyvinyl chloride plant, said apparatus comprising the elements A) at least one high-boilers column in the plant component dedicated to the distillative purification of 1,2-dichloroethane where substances boiling higher than 1,2-dichloroethane are removed, B) at least one heat exchanger which is connected to the high-boilers column and into which at least part of the overhead stream from the high-boilers column is conveyed to be condensed and optionally supercooled therein to obtain heat by generating low-pressure steam and then to be returned into the high-boilers column, and C) at least one heatsink of a component plant for production of 1,2-dichloroethane and/or in an attached component plant for production of vinyl chloride and/or in an attached component plant for production of polyvinyl chloride, into which the low-pressure steam generated in heat exchanger B) is conveyed for heating purposes.

The heatsinks used in the parts of the VCM complex and/or of the PVC plant are preferably the apparatuses described above.

The process of the present invention or the apparatus of the present invention provides a distinct improvement in the energy balance of the plant complex.

What is claimed is:

1. A process for the capture and use of excess heat recovered during the production of vinyl chloride by the thermal cleavage of 1,2-dichloroethane in a vinyl chloride manufacturing complex that incorporates distillative purification of 1,2-dichloroethane using at least one high-boilers column in which substances boiling at temperatures higher than the boiling point of 1,2-dichloroethane are removed, the process comprising:

distillatively purifying 1,2-dichloroethane by boiling 1,2-dichloroethane at temperatures between 120-150° C. in a high-boilers column of the vinyl chloride manufacturing complex to create a 1,2-dichloroethane vapor stream;

capturing thermal energy from at least a portion of a distillatively purified 1,2-dichloroethane vapor stream, by at least one heat exchanger associated with at least one of a plant component dedicated to producing 1,2-dichloroethane, a downstream plant component dedicated to producing vinyl chloride, or a downstream plant component dedicated to producing polyvinyl chloride;

generating low-pressure steam from the thermal energy captured by the heat exchanger;

returning the 1,2-dichloroethane vapor into the high-boilers column following a condensation thereof; and heating selected parts of the plant with the generated low pressure steam.

2. The process of claim 1, wherein the at least one heat exchanger used in capturing thermal energy is a falling-stream evaporator, plate-type heat exchanger, coil-type heat exchanger, or tube-bundle heat exchanger, the tube-bundle heat exchanger being fitted with tubes specifically suitable for heat exchange at low temperature differences.

3. The process of claim 1, further comprising:
by the generated low pressure steam, heating heat sinks in at least one of a downstream vinyl chloride monomer manufacturing plant or a downstream polyvinyl chloride manufacturing plant.

4. The process of claim 3, further comprising:
by the generated low pressure steam, heating at least one of the following manufacturing plant components from the vinyl chloride manufacturing complex: a dewatering column, a low-boilers column, a DCE stripper, a vacuum column, a boiler feed water devolatilizer, a stripping column for removing 1,2-dichloroethane from wastewater, and a stripping column for purifying or removing hydrogen chloride from the vinyl chloride.

5. The process of claim 3, further comprising:

by the generated low pressure steam, heating at least one of the following manufacturing plant components from the polyvinyl chloride manufacturing plant: apparatuses for removing residual monomer from polyvinyl chloride, a predevolatilizing device, a downstream devolatilizing column, a stripping column for removing vinyl chloride monomer from wastewater, an apparatus for drying PVC powder, and an apparatus for heating batch water for the polymerization reaction.

6. The process of claim 1, wherein the high-boilers column is continuously operated for a period of time between six and twenty-four months.

7. An apparatus for production of vinyl chloride by thermal cleavage of 1,2-dichloroethane in a vinyl chloride manufacturing complex incorporating a distillative purification of 1,2-dichloroethane, said apparatus comprising:

a first manufacturing plant configured to distillatively purify 1,2-dichloroethane in which substances having a higher boiling temperature than 1,2-dichloroethane are removed;

at least one high-boilers column disposed in said manufacturing plant dedicated to the distillative purification of 1,2-dichloroethane, and configured to generate a 1,2-dichloroethane vapor stream;

at least one heat exchanger in communication with said high-boilers column that is configured to collect heat, and generate low-pressure steam, from at least a portion of the generated 1,2-dichloroethane vapor stream, and further configured to condense the 1,2-dichloroethane vapor stream and return the condensed vapor stream to the high-boilers column; and at least one of a second manufacturing plant configured to produce 1,2-dichloroethane, vinyl chloride, or polyvinyl chloride, said second manufacturing plant in communication with said at least one heat exchanger;

at least one heat sink disposed in said at least one second manufacturing plant into which heat sink the low-pressure steam generated by said at least one heat exchanger is conveyed for heating at least one component of the vinyl chloride manufacturing complex.

8. The apparatus of claim 7, wherein said heat exchanger is further configured to supercool the 1,2-dichloroethane vapor stream conveyed to it by said high boilers column.

9. The apparatus of claim 7, wherein said heat sink is disposed in a component plant of the vinyl chloride manufacturing complex and is a dewatering column, a low-boilers column, a DCE stripper, a vacuum column, a boiler feed water devolatilizer, a stripping column for removing 1,2-dichloroethane from wastewater, or a stripping column for purifying or removing hydrogen chloride from the vinyl chloride.

10. The apparatus of claim 7, wherein the heat sink is disposed in a polyvinyl chloride manufacturing plant and is an apparatus for removing residual monomer from polyvinyl chloride, a predevolatilizing device and a downstream devolatilizing column, a stripping column for removing vinyl chloride monomer from wastewater, an apparatus for drying polyvinyl chloride powder, or an apparatus for heating batch water for use in a polymerization reaction.

11. The apparatus of claim 7, wherein the heat exchanger is a falling-stream evaporator, a plate-type heat exchanger, a coil-type heat exchanger, or a tube-bundle heat exchanger, the tube-bundle heat exchanger being fitted with tubes configured for heat exchange at low temperature differences.

* * * * *